United States Patent

Suwa et al.

(10) Patent No.: US 8,969,820 B2
(45) Date of Patent: Mar. 3, 2015

(54) RADIOGRAPHIC APPARATUS

(71) Applicant: Canon Kabushiki Kaisha, Tokyo (JP)

(72) Inventors: Hidetomo Suwa, Machida (JP); Akio Saigusa, Tama (JP); Tetsuo Watanabe, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/907,450

(22) Filed: May 31, 2013

(65) Prior Publication Data

US 2013/0266121 A1 Oct. 10, 2013

Related U.S. Application Data

(62) Division of application No. 13/061,796, filed as application No. PCT/JP2010/058487 on May 13, 2010.

(30) Foreign Application Priority Data

Jun. 5, 2009 (JP) ................................. 2009-136711

(51) Int. Cl.
*H01L 27/146* (2006.01)
*G01T 1/24* (2006.01)
(Continued)

(52) U.S. Cl.
CPC ................ *G01T 1/24* (2013.01); *A61B 6/4405* (2013.01); *A61B 6/4411* (2013.01); *G03B 42/04* (2013.01)
USPC ................ 250/370.09; 250/370.01; 250/371; 250/378

(58) Field of Classification Search
USPC .......................... 250/370.09, 370.01–371, 378
See application file for complete search history.

(56) References Cited

U.S. PATENT DOCUMENTS 6,667,480 B2 * 12/2003 Kajiwara et al. .......... 250/370.01
7,104,686 B2 9/2006 Watanabe et al. ............. 378/189
(Continued)

FOREIGN PATENT DOCUMENTS

CN 1540364 10/2004
JP 2001-099942 4/2001
(Continued)

OTHER PUBLICATIONS

International Search Report dated Aug. 17, 2010, issued in International Application No. PCT/JP2010/058487.
(Continued)

*Primary Examiner* — David Porta
*Assistant Examiner* — Abra Fein
(74) *Attorney, Agent, or Firm* — Fitzpatrick, Cella, Harper & Scinto (57) ABSTRACT

A radiographic apparatus includes an X-ray detection sensor having a two-dimensional detector plane for detecting an intensity distribution of X-rays, a body internally containing the X-ray detection sensor, a supporting member having a supporting surface for supporting the X-ray detection sensor across the detector plane and which fixes the X-ray detection sensor to an inner bottom surface of the body, and a circuit board on which is mounted a circuit for reading out a detection signal from the X-ray detection sensor. Furthermore, in the radiographic apparatus, the supporting member forms a space between the supporting member and the inner bottom surface of the body in a peripheral portion of the supporting member. At least a part of the circuit board is arranged in the space.

14 Claims, 8 Drawing Sheets

A-A CROSS SECTION (51) Int. Cl.
*A61B 6/00* (2006.01)
*G03B 42/04* (2006.01)

(56) References Cited

U.S. PATENT DOCUMENTS

| | | | |
|---|---|---|---|
| 7,112,800 B2 | 9/2006 | Sato et al. | 250/370.09 |
| 7,495,226 B2 | 2/2009 | Jadrich et al. | 250/370.09 |
| 7,537,385 B2 * | 5/2009 | Watanabe et al. | 378/189 |
| 7,582,879 B2 | 9/2009 | Abenaim et al. | 250/370.11 |
| 7,734,016 B2 | 6/2010 | Watanabe | 378/145 |
| 7,889,843 B2 | 2/2011 | Watanabe | 378/116 |
| 7,924,982 B2 | 4/2011 | Watanabe | 378/114 |
| 7,959,355 B2 | 6/2011 | Stantchev | 378/191 |
| 2003/0026382 A1 | 2/2003 | Takeda | 378/19 |
| 2007/0272873 A1 | 11/2007 | Jadrich et al. | 250/370.11 |
| 2010/0254517 A1 | 10/2010 | Watanabe | 378/154 |

FOREIGN PATENT DOCUMENTS

| | | |
|---|---|---|
| JP | 2002-158341 A | 5/2002 |
| JP | 2003-014855 | 1/2003 |
| JP | 3382227 | 3/2003 |
| JP | 2003-121553 | 4/2003 |
| JP | 2003-248060 | 9/2003 |
| JP | 2004-327825 | 11/2004 |
| JP | 2007-199079 | 8/2007 |
| JP | 4078096 | 4/2008 |
| JP | 4393528 | 1/2010 |

OTHER PUBLICATIONS

Office Action dated Apr. 11, 2013, issued in counterpart Chinese(PRC) Patent Application No. 201080024836.5, with translation.

* cited by examiner

A-A CROSS SECTION

FIG. 3B

B-B CROSS SECTION

FIG. 4A

A-A CROSS SECTION

FIG. 4B

B-B CROSS SECTION

FIG. 5A

A-A CROSS SECTION

FIG. 5B

B-B CROSS SECTION

FIG. 6A

A-A CROSS SECTION

FIG. 6B

B-B CROSS SECTION

RADIOGRAPHIC APPARATUS

RELATED APPLICATIONS

The present application is a divisional of application Ser. No. 13/061,796, filed Mar. 2, 2011, which is a National Stage filing under 35 U.S.C. §371 of International Application No. PCT/JP2010/058487, filed May 13, 2010. The present application claims benefit of parent application Ser. No. 13/061, 796 (PCT/JP2010/058487) under 35 U.S.C. §120, and claims priority benefit under 35 U.S.C. §119 of Japanese Patent Application 2009-136711, filed Jun. 5, 2009. The entire contents of each of the mentioned prior applications are incorporated herein by reference.

BACKGROUND

1. Technical Field

The present invention relates to a radiographic apparatus using a solid-state imaging device.

2. Background Art

Apparatuses that irradiate an object with X-rays and detect an intensity distribution of X-rays transmitted through the object to obtain a radiographic image of the object are widely used in industrial nondestructive testing and in medical diagnosis. Commonly used methods of such photography include a film/screen method for X-rays. The film/screen method involves performing photography by combining a photographic sensitive film with phosphor that is X-ray sensitive. Phosphor, a rare earth that emits light when irradiated by X-rays, is formed into a sheet and appressed against both faces of a photographic sensitive film. X-rays transmitted through an object are converted into visible light by the phosphor, whereby the light is captured by the photographic sensitive film. Visualization is achieved by developing a latent image formed on the film by chemical processing.

Moreover, recent progresses in digital technology has led to the widespread use of a method where an intensity distribution of X-rays transmitted through an object is converted into and detected as an electric signal, whereby the electric signal is processed and reproduced on a monitor or the like as a visible image to obtain a high-definition radiographic image. As a method for converting such a radiographic image into an electric signal, a radiographic image recording/reproducing system has been proposed in which X-rays transmitted through an object are temporarily accumulated in phosphor as a latent image and an excitation light such as laser light is subsequently irradiated to photoelectrically read out and output the latent image as a visible image.

Furthermore, with recent progress in semiconductor process technology, apparatuses that photograph a radiographic image in the same manner using a semiconductor sensor have been developed. Such systems have a significantly wider dynamic range than conventional X-ray photography systems using a photographic sensitive film and are pragmatically advantageous in that radiographic images not affected by variances in an amount of X-ray exposure can be obtained. At the same time, unlike conventional photographic sensitive film systems, chemical processing is not required. Accordingly, there is another advantage that output images can be obtained instantaneously. Such systems are advantageous in that, unlike the aforementioned radiographic image recording/reproducing systems that read out images in a subsequent process, images can be instantaneously displayed on a monitor. Furthermore, portable radiographic apparatuses have also been developed and are used in situations that require photographs to be taken in arbitrary shooting postures.

In regards to such a portable radiographic apparatus, Japanese Patent No. 3382227 (hereinafter referred to as Document 1) proposes a structure in which boards (substrates) and the like are laminated in an X-ray incidence direction of an X-ray detection sensor for purposes of thinning and weight saving. In addition, Japanese Patent Laid-Open No. 2003-014855 (hereinafter, Document 2) proposes achieving weight saving in a portable radiographic apparatus by laminating boards and the like in an X-ray incidence direction and reducing use of an X-ray shielding member (having a high specific gravity) that protects the boards from X-rays.

Generally, increasing an intrinsic strength of an apparatus while protecting the inside of the apparatus results in the apparatus itself becoming heavier and bigger. With a portable radiographic apparatus, there may be cases where photography is performed by inserting the apparatus under a subject, such as photography of a subject on a table in an X-ray room, a subject on a ward bed, or a subject on an operating table in an operating room. Therefore, in the interest of reducing the strain on patients, thinning of portable radiographic apparatuses is required. In addition, when inserting a radiographic apparatus under a subject during photography, an X-ray technician operating the radiographic apparatus is required to hold the apparatus with one hand. In particular, when a radiographic apparatus is used at the bedside in wards by a technician making ward rounds on a visiting car, the technician must set the radiographic apparatus while single-handedly maintaining the posture of a patient. Therefore, downsizing and weight saving are essential in order to similarly reduce the strain on technicians as well. As seen, portable radiographic apparatuses are faced with issues that conflict with the perspective of protecting the apparatus, namely, thinning from the perspective of reducing the strain on patients and weight saving from the perspective of reducing the strain on operators.

However, with the apparatus cited in Document 1, a board for driving a sensor, a board for processing a signal acquired by an X-ray detection sensor, and the like are all arranged on an underside. Therefore, there is a limit to how much the thickness of the radiographic apparatus itself can be reduced. In addition, a photographic unit itself must be strong enough to protect the X-ray detection sensor from external force. However, in the structure proposed in Document 1, since a portion in which the boards are arranged becomes a space, strength declines. Maintaining strength requires reinforcement such as inserting a member having a predetermined strength to an underside of the X-ray detection sensor. Consequently, a limit is posed with respect to achieving thinning.

Furthermore, with the apparatus proposed in Document 2, a drive circuit board and a signal processing circuit board for processing a signal obtained from a sensor are arranged in parallel with respect to an X-ray detection sensor. As a result, unlike Document 1, thinning can be realized. However, since boards are arranged in a planar direction, a limit is posed with respect to downsizing.

SUMMARY OF INVENTION

The present invention has been made in consideration of the problems described above, and according to an embodiment of the present invention, a radiographic apparatus is provided which realizes weight saving, downsizing and thinning while protecting an interior X-ray detection sensor from external load and impact.

According to one aspect of the present invention, there is provided a radiographic apparatus comprising a X-ray detection sensor having a detector plane for detecting an X-ray, a read circuit board which reads out a detection signal from the X-ray detection sensor, a body which contains the X-ray detection sensor, a plate-like base which supports the X-ray detection sensor, and a structural body which supports the base against an inner bottom surface of the body, in which a first space is formed inside of a projection plane of the X-ray detection sensor as viewed from an X-ray incidence direction and between the inner bottom surface of the body and a surface on an opposite side to a supporting surface of the X-ray detection sensor in the base, and in which the read circuit board is arranged in the first space.

Further features of the present invention will become apparent from the following description of exemplary embodiments with reference to the attached drawings.

DESCRIPTION OF EMBODIMENTS

Hereinafter, embodiments of the present invention will be described in detail with reference to the attached drawings.

[First Embodiment]

Figure 1:
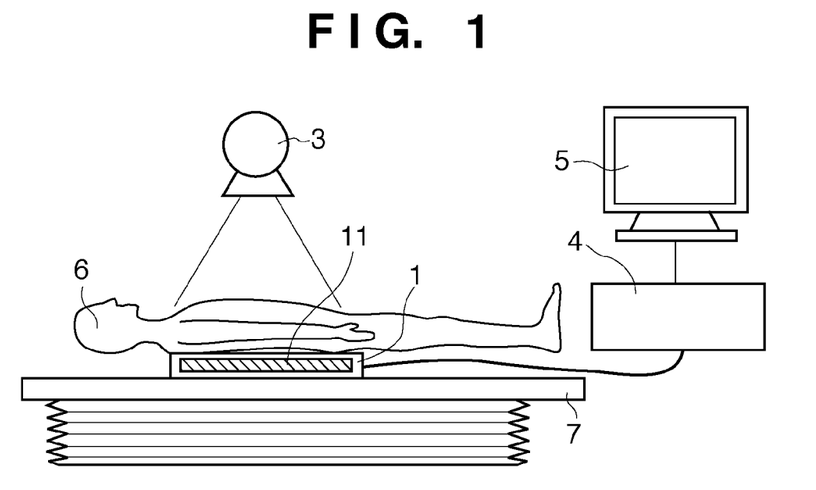
FIG. 1 is a diagram illustrating an example of usage of an apparatus.

FIG. 1 presents a conceptual diagram of a system using a radiographic apparatus according to a first embodiment. A radiographic apparatus 1 has a built-in X-ray detection sensor 11 having a two-dimensional detector plane for detecting an X-ray intensity distribution. In addition, an X-ray generator 3 is provided above the radiographic apparatus 1 and irradiates X-rays on a subject 6 on an examination table 7. X-rays transmitted through the subject 6 are converted into visible light via phosphor at the X-ray detection sensor 11 and detected as an electric signal by photoelectric conversion elements arranged in a two-dimensional grid. The radiographic apparatus 1 is configured to include a control unit for controlling read driving, image transfer, and the like. An image output from the radiographic apparatus 1 is subjected to digital image processing by an image processing apparatus 4 and displayed as a radiographic image of the subject 6 on a monitor 5.

Figure 2:
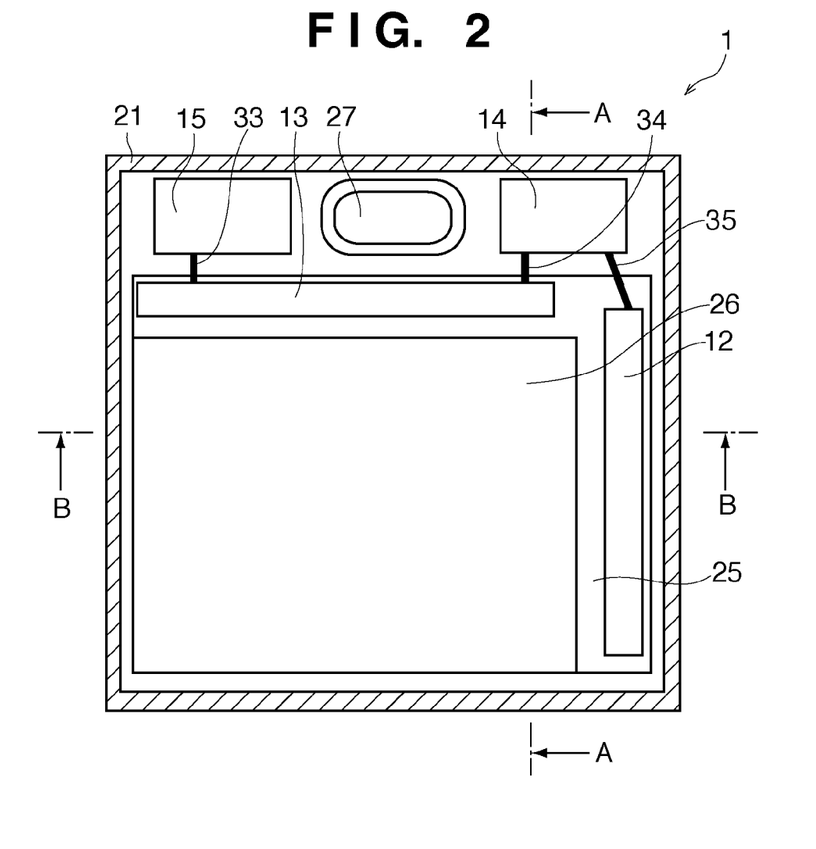
FIG. 2 is a diagram illustrating a configuration of an X-ray detection sensor according to a first embodiment.
Figure 3A:
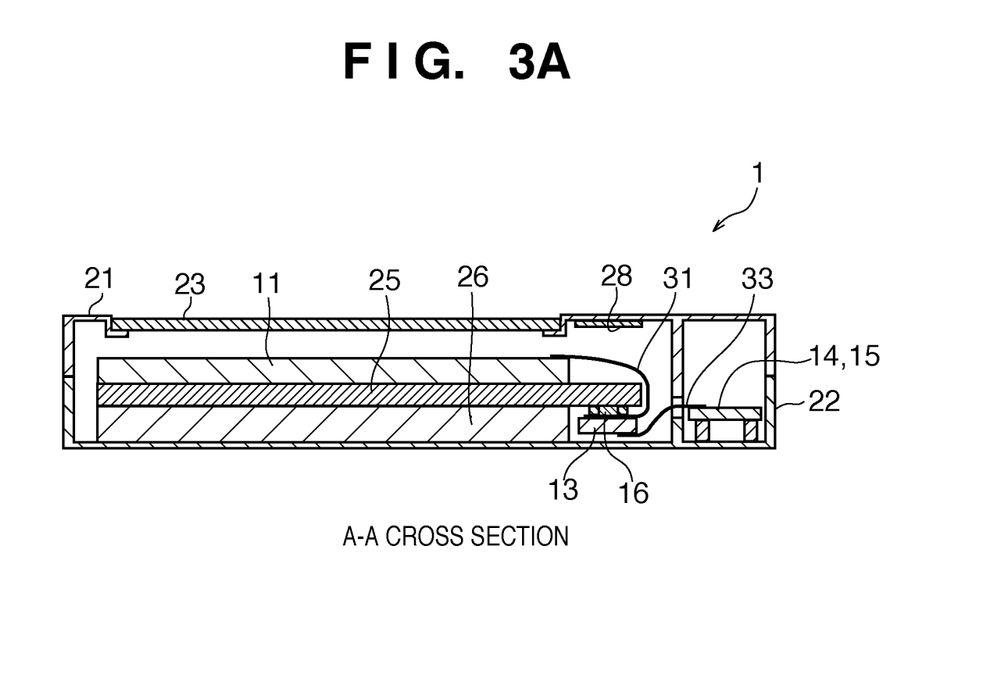
FIGS. 3A and 3B are cross-sectional views illustrating the configuration of the X-ray detection sensor according to the first embodiment.

FIG. 2 is a diagram illustrating an arrangement of boards and the like inside a body when the radiographic apparatus 1 is viewed from an opposite side with respect to an X-ray incidence direction. FIG. 3A is a cross-sectional view taken along A-A in FIG. 2. In FIG. 2 and FIG. 3A, a body 21 is a first body on an X-ray incidence side covering the X-ray detection sensor. The body 21 is made of a material that is light-weight, high-strength, and rigid such as an aluminum alloy or a magnesium alloy, and protects the X-ray detection sensor 11. In order to acquire a high-quality image with a high S/N ratio, X-rays irradiated from an X-ray tube and transmitted through the subject must be allowed to reach the X-ray detection sensor 11 without waste. Therefore, a high radiolucency is required on an X-ray incidence-side projection plane of the X-ray detection sensor 11 in the body 21. To this end, an X-ray transmitting member 23 is arranged as an upper panel on the X-ray incidence-side projection plane of the body 21. In the present example, CFRP that is carbon fiber reinforced plastic with a high radiolucency is adopted at an X-ray incidence unit and bonded to the body 21 by an adhesive. The detector plane of the X-ray detection sensor 11 is fixed so as to oppose, inside the body, the X-ray transmitting member 23 that is the upper panel. A body 22 is a second body on an opposite side to the X-ray incidence side that covers the X-ray detection sensor. In the same manner as the body 21, the body 22 is made of a material that is light-weight, high-strength, and rigid such as an aluminum alloy or a magnesium alloy.

The X-ray detection sensor 11 is contained inside a box-shaped body formed by the body 21 and the body 22, and protected from external stress or the like. The X-ray detection sensor 11 is arranged so that the detector plane thereof opposes the X-ray transmitting member 23. The X-ray detection sensor 11 has a laminated configuration constituted by an aluminum sheet that protects the phosphor from the X-ray incidence side, the phosphor that converts radioactive rays into visible light, photoelectric conversion elements arranged in a grid that convert visible light into an electric signal, and a board having the photoelectric conversion elements formed on a surface thereof.

Since the board of the X-ray detection sensor 11 is formed of a material such as glass, the X-ray detection sensor 11 cannot be directly fixed to the body by, for example, fastening using screws. Therefore, some kind of a supporting member is required to fix the X-ray detection sensor 11 to the body. In the present embodiment, the supporting member is fixed to a lower panel opposing the upper panel of the body and fixes the X-ray detection sensor 11 so that the detector plane and the upper panel oppose each other. In the present embodiment, the supporting member is constituted by a base 25 and a structural body 26. The base 25 that supports the X-ray detection sensor 11 is a plate-like member having a supporting surface that supports the X-ray detection sensor 11 from the underside (the side opposite to the X-ray incidence side) of the detector plane. The supporting surface and the underside surface of the X-ray detection sensor are bonded by a sticky material or the like. The base 25 is a plate-like metallic member made of a material that is light-weight, high-strength, and rigid such as an aluminum alloy or a magnesium alloy, and has a structure for determining a position relative to the body. In order to realize thinning, the base 25 is not provided with a bending strength enabling sufficient protection of the X-ray detection sensor 11 from external stress. To protect the X-ray detection sensor 11 from external forces, the structural body 26 with sufficient rigidity is arranged on a side opposite to the X-ray incidence side of the base 25, thereby constituting a structure that supports the base 25 against the lower panel (inner bottom surface) of the body. Accordingly, when an external load is applied to the side of the body 21 such as when mounted by a subject, load-bearing is shared by the structural body 26 and the body 22 to enable protection of the X-ray detection sensor 11.

Figure 4A:
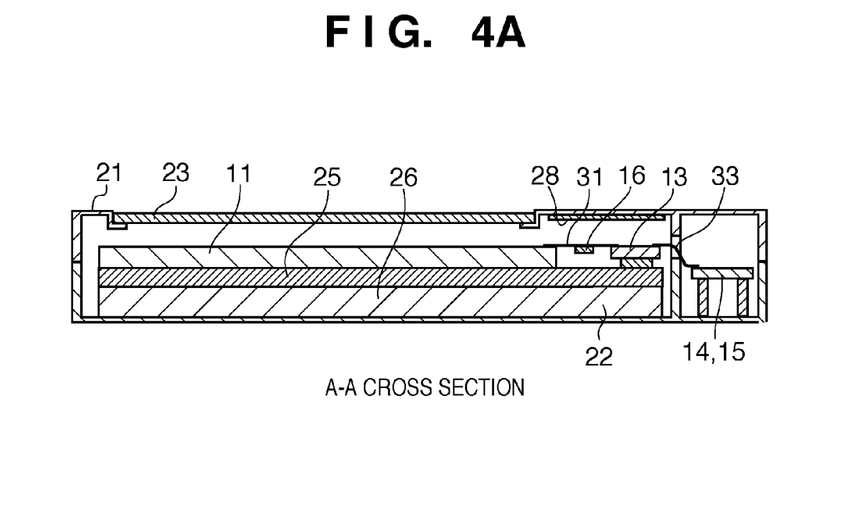
FIGS. 4A and 4B are cross-sectional views illustrating a configuration of a general X-ray detection sensor.

As X-rays are irradiated, a radiological image converted into an electric signal by the photoelectric conversion elements in the X-ray detection sensor 11 is sent to a read circuit board 13 via a flexible wiring board 31 on which is mounted a signal processing IC 16. An X-ray shielding member 28 is arranged on the X-ray incidence side of the read circuit board 13. Accordingly, the read circuit board 13 is protected from X-rays. In addition, by locally providing an X-ray shielding member in this manner, weight saving of the apparatus can be achieved. The read circuit board 13 is arranged on a surface both outside of a projection plane of the X-ray detection sensor 11 as viewed from an X-ray incidence direction and on a side opposite to the X-ray incidence side of the base 25, and is fixed by screws or the like to a fastening unit provided on the base 25. Such an arrangement electromagnetically shields the read circuit board 13 and enables acquisition of high-quality images with high S/N ratios. In addition, while the size of the apparatus increases by extending the flexible wiring board 31 as illustrated in FIG. 4A, the apparatus can be downsized by folding or bending the read circuit board 13. Furthermore, downsizing of the apparatus reduces the amount of material used for the body and enables weight saving.

Figure 3B:
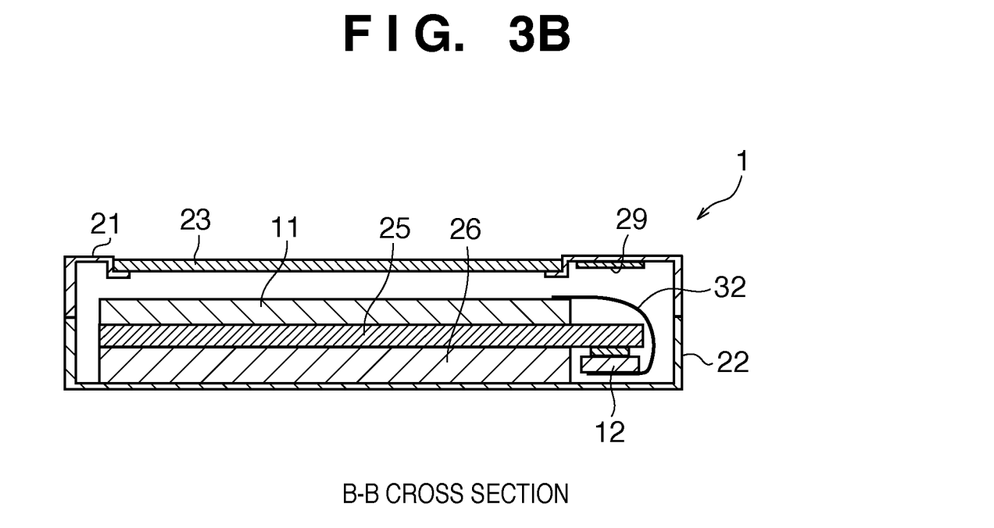
Figure 4B:
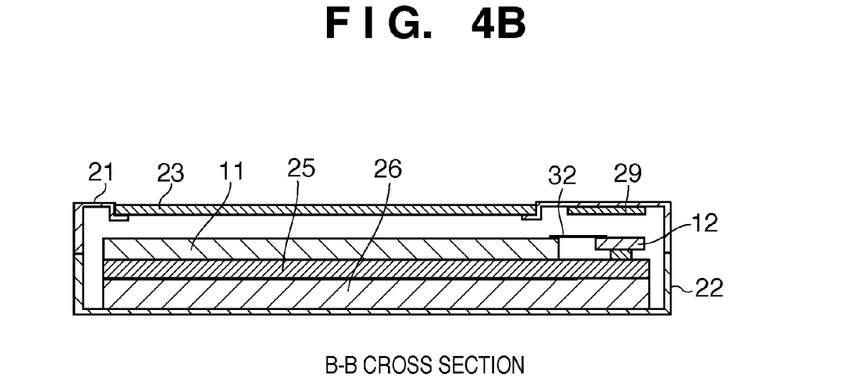

FIG. 3B is a cross-sectional view of the radiographic apparatus 1 taken along B-B in FIG. 2. A drive circuit board 12 functions to control driving of the X-ray detection sensor 11 using power supplied from a power circuit board 14 as a power unit. The drive circuit board 12 is arranged on a surface both outside of a projection plane of the X-ray detection sensor 11 as viewed from an X-ray incidence direction and on a side opposite to the X-ray incidence side of the base 25, and is fixed by screws or the like to a fastening unit provided on the base 25. An X-ray shielding member 29 is arranged on an X-ray incidence side of the drive circuit board 12. Accordingly, the drive circuit board 12 is protected from X-rays. In addition, while the size of the apparatus increases by extending a flexible wiring board 32 as illustrated in FIG. 4B, downsizing and weight saving of the apparatus can be achieved by arranging the drive circuit board 12 by folding or bending the flexible wiring board 32.

In FIG. 3A, a signal read out by the read circuit board 13 is sent via a cable 33 to a signal processing circuit board 15 as a signal processing unit. The signal processing circuit board 15 and the power circuit board 14 are arranged in a planar direction on a side of the read circuit board 13 of the X-ray detection sensor 11 and are respectively connected to the drive circuit board 12 and the read circuit board 13 by cables 33, 34, and 35. Accordingly, cable lengths between boards can be minimized and space necessary for cable wiring can also be minimized As a result, downsizing and weight saving of the apparatus can be achieved.

Moreover, a handle unit 27 to be used during operation and transportation of the apparatus is provided on the bodies 21 and 22 on the side of the read circuit board 13 of the X-ray detection sensor 11. As illustrated, the handle unit 27 is provided in a region of the body in which the supporting member does not exist, and is to be used when a user transports the apparatus. The power circuit board 14 and the signal processing circuit board 15 are separately arranged so as to sandwich the handle unit 27. By adopting such an arrangement that effectively uses spaces on both sides of a handle, an increase in size of the apparatus can be suppressed even when the power circuit board 14 and the signal processing circuit board 15 are arranged in a planar direction with respect to the X-ray detection sensor 11. As a result, downsizing and weight saving can be achieved. In addition, by arranging the power circuit board 14 and the signal processing circuit board 15 with the handle in-between, the effect of noise or the like generated by the power circuit board 14 on the signal processing circuit board 15 can be suppressed.

As seen, in the configuration of the radiographic apparatus according to the first embodiment, the size of the base 25 is arranged so as to be greater than bonding surfaces to the X-ray detection sensor 11 and the structural body 26. In addition, at a portion where the base 25 protrudes from the structural body 26, a space is formed between the underside surface of the base 25 and the lower panel (inner bottom surface) of the body. Circuit boards for driving the X-ray detection sensor 11 and reading out detection signals are to be contained in the space. In other words, a space is formed between the base 25 and the inner bottom surface in a peripheral portion of a supporting member that includes the base 25 and the structural body 26, whereby at least a part of the circuit boards is to be contained in the space. In the present embodiment, the read circuit board 13 and the drive circuit board 12 have been described as examples of such circuit boards. Consequently, downsizing and weight saving of the apparatus can be achieved while retaining strength for protecting the X-ray detection sensor and, for example, convenience as a cassette can be improved.

[Second Embodiment]

Figure 5A:
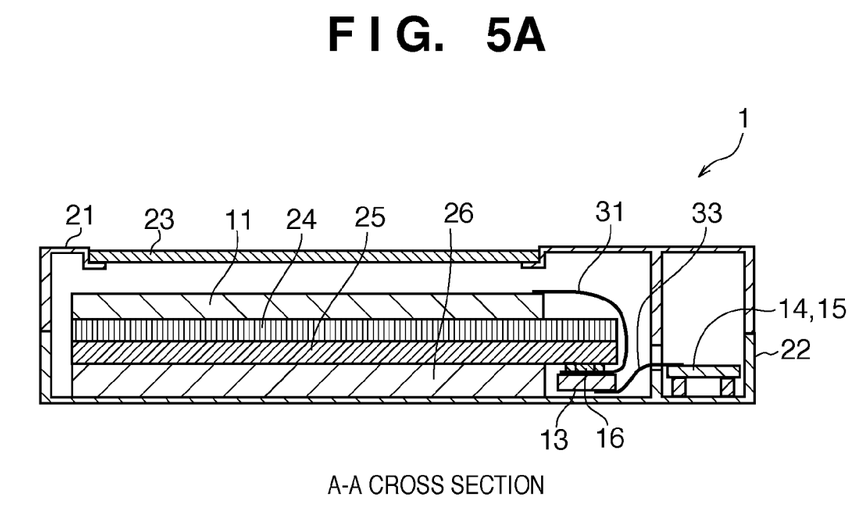
FIGS. 5A and 5B are cross-sectional views illustrating a configuration of an X-ray detection sensor according to a second embodiment.
Figure 5B:
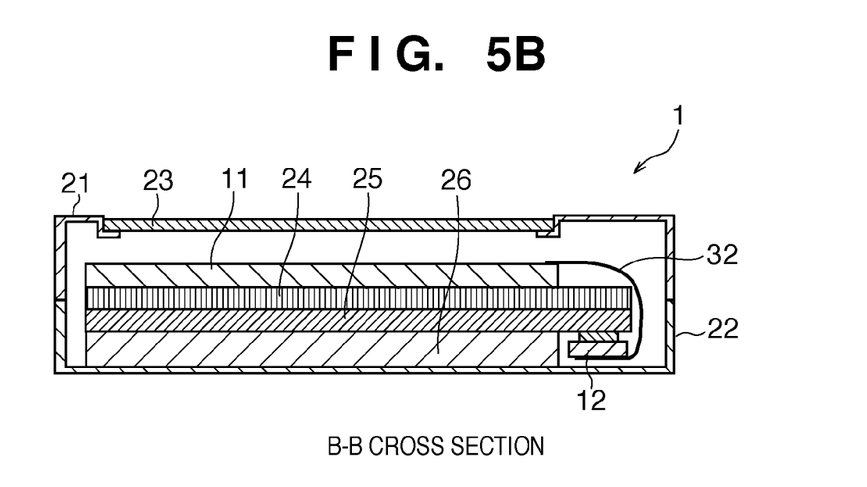

For the first embodiment, a configuration has been described where X-ray shielding members 28 and 29 are locally provided. In a second embodiment, a configuration will be described in which an X-ray shielding member for shielding scattered radiation from behind is arranged across an entire supporting surface of a base 25, whereby the X-ray shielding member doubles as an X-ray shielding member for circuit boards. FIGS. 5A and 5B are diagrams illustrating a configuration of a radiographic apparatus 1 according to the second embodiment. The radiographic apparatus according to the second embodiment represents an example where, to the configuration according to the first embodiment (FIGS. 3A and 3B), an X-ray shielding member 24 for preventing the effect of scattered radiation from behind has been inserted between the X-ray detection sensor 11 and the base 25. A heavy metal such as lead or molybdenum is used as the X-ray shielding member 24. As illustrated in FIG. 5A, the X-ray shielding member 24 has a greater projected area than the X-ray detection sensor 11, and covers up to a portion of a read circuit board 13. Accordingly, the read circuit board 13, a part of a flexible wiring board 31, and a signal processing IC 16 can be protected from X-rays without requiring the X-ray shielding member 28 (FIG. 3A). In addition, in the same manner as the first embodiment, arranging the read circuit board 13 by folding or bending the flexible wiring board 31 instead of extending the same enables downsizing and weight saving of the apparatus to be achieved.

Similarly, the X-ray shielding member 24 inserted between the X-ray detection sensor 11 and the base 25 in FIG. 5B covers up to a portion of a drive circuit board 12. Accordingly, the drive circuit board 12 and a part of a flexible wiring board 32 can be protected from X-rays without requiring the X-ray shielding member 29 (FIG. 3B). In addition, arranging the drive circuit board 12 by folding or bending the flexible wiring board 32 instead of extending the same enables downsizing of the apparatus to be achieved.

[Third Embodiment]

In the first and second embodiments, the size of the base 25 is arranged so as to be greater than bonding surfaces to the X-ray detection sensor 11 and the structural body 26. For a third embodiment, a configuration will be described in which the size of the base 25 is equal to the size of the X-ray detection sensor 11.

Figure 6A:
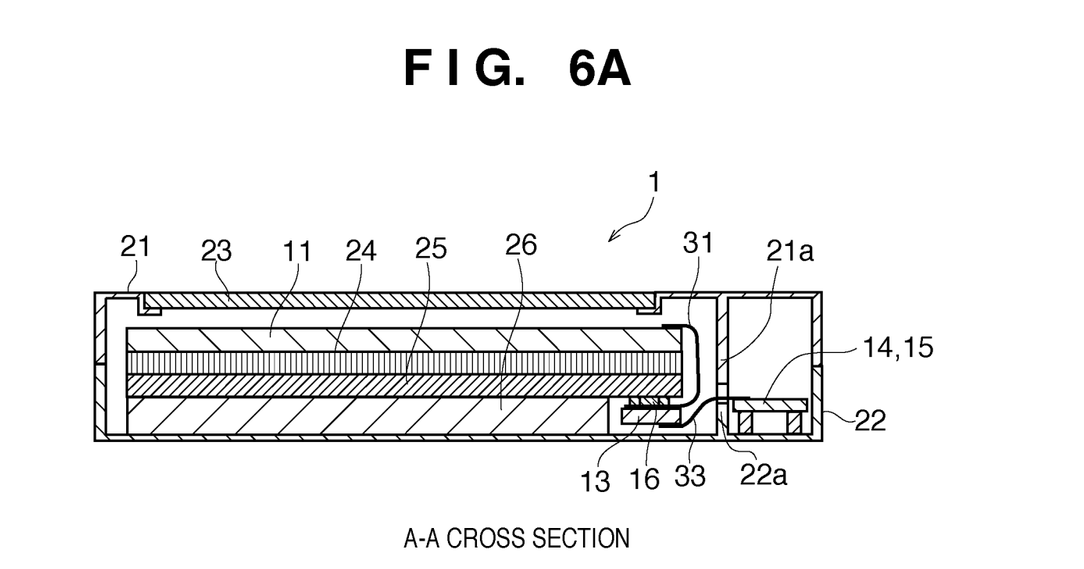
FIGS. 6A and 6B are cross-sectional views illustrating a configuration of an X-ray detection sensor according to a third embodiment.
Figure 6B:
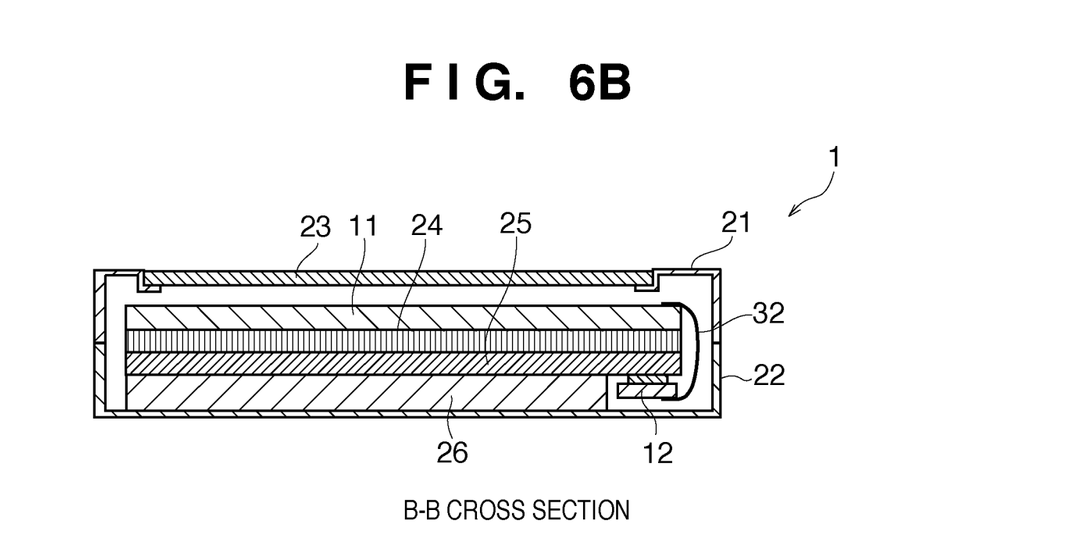
Figure 7:
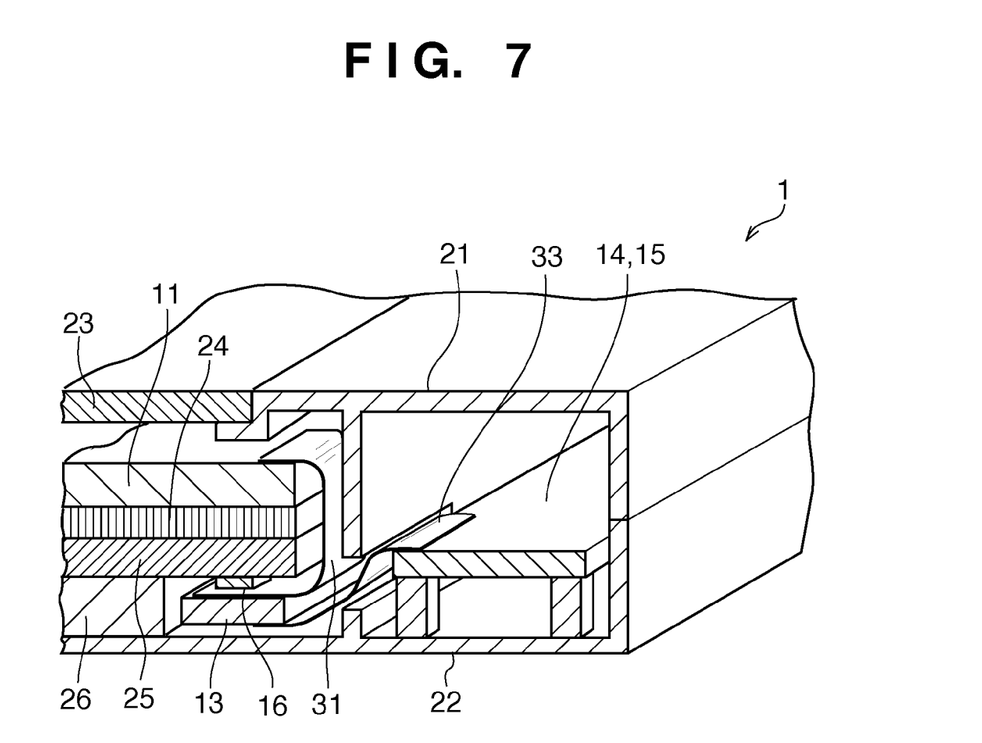
FIG. 7 is a perspective view that is a partial enlargement of FIG. 6A according to the third embodiment.

An arrangement of boards and the like inside a body when viewing a radiographic apparatus 1 according to the third embodiment from a side opposite to an X-ray incidence direction is similar to the first embodiment (FIG. 2). However, there is a difference in a magnitude relationship between the base 25, the X-ray detection sensor 11, and the structural body 26. FIG. 6A is a cross-sectional view taken along A-A in FIG. 2, and FIG. 6B is a cross-sectional view taken along B-B in FIG. 2. In addition, FIG. 7 is a perspective view that is an enlargement of a vicinity of a read circuit board 13 illustrated in FIG. 6A. In FIG. 6A, on one side of the X-ray detection sensor 11 on the read circuit board 13 side, the structural body 26 is retreated to the inside of a projection plane of the X-ray detection sensor 11 as viewed from an X-ray incidence direction. The read circuit board 13 is arranged in the retreat space and fastened to a fastening unit provided on the base 25 by screws and the like.

However, when the structural body 26 is retreated in this manner, there is a risk that the strength of the retreat space portion declines. In addition, since a flexible wiring board 31 includes a signal processing IC 16 mounted thereon, the board tends to become longer. An arrangement in which the flexible wiring board 31 is extended increases the size of the retreat space and a further decline in strength is anticipated. Therefore, as illustrated in FIG. 7, the flexible wiring board 31 is folded or bent and the signal processing IC 16 is sandwiched between and fixed by the read circuit board 13 and the base 25. Accordingly, the retreat space can be reduced and a decline in strength can be suppressed. In addition, the signal processing IC 16 itself can now be protected from X-rays by an X-ray shielding member 24. Furthermore, since the signal processing IC 16 does not have to be fixed by a separate part and can be maintained in a stable state in a body, a reduction of the number of parts can also be achieved. In this case, the thickness of the structural body in the X-ray incidence direction must be increased so as to exceed the sum of thicknesses of the read circuit board 13, the flexible wiring board 31, and the signal processing IC 16 mounted on the flexible wiring board 31 (this condition also applies to the first and second embodiments).

Figure 8A:
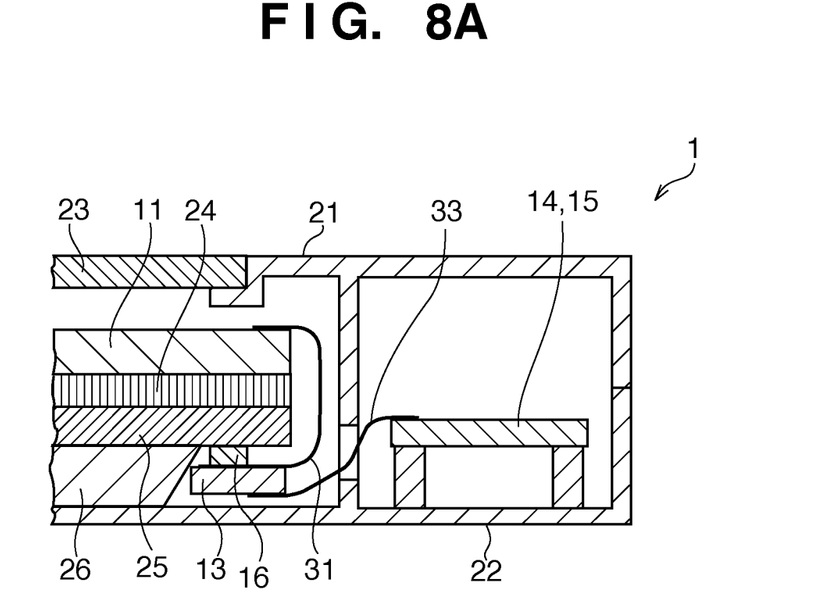
FIGS. 8A and 8B are cross-sectional views illustrating a configuration of the X-ray detection sensor according to the third embodiment.
Figure 8B:
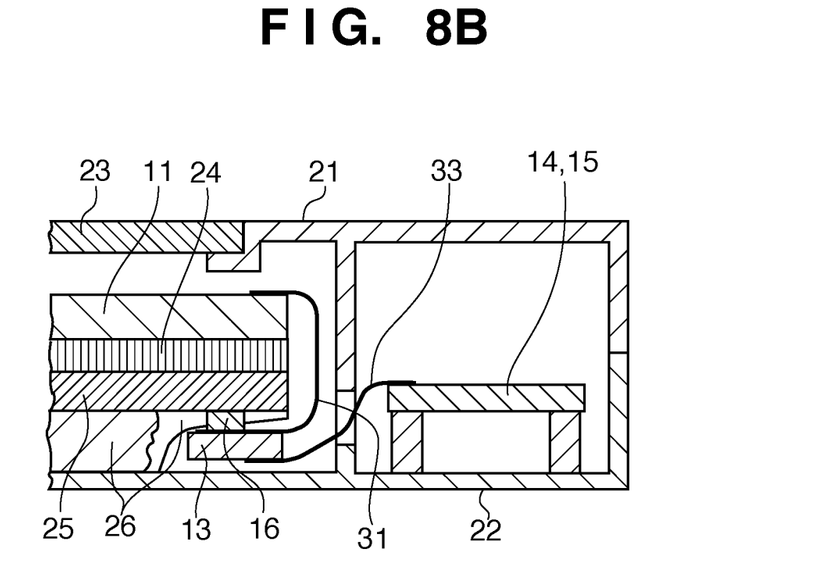

In addition, as illustrated in FIG. 8A or 8B, a part of the structural body 26 may be retained so as to suppress a decline in the strength of the retreat space. In FIG. 8A, an area in which the structural body 26 supports the base 25 is increased by inclining a wall face of the structural body 26. Furthermore, in FIG. 8B, the retreat space is reinforced by extending the structural body 26 towards an edge of the base 25 so as not to interfere with the plurality of signal processing ICs 16 that discretely exist in a depth direction of the drawing. Moreover, by positioning a first body 21 as close as possible in a range not entering an effective range of the X-ray detection sensor 11 and providing walls 21a and 22a in a vicinity of the retreat space as illustrated in FIG. 6A, loads can be supported by the body 21 and a body 22. Accordingly, even when a load is applied to the apparatus when, for example, mounted by a subject 6, further downsizing of the apparatus can be achieved while protecting the X-ray detection sensor 11.

Furthermore, as illustrated in FIG. 6B, the structural body 26 is also retreated on one side on the drive circuit board 12 side to the inside of a projection plane of the X-ray detection sensor 11 as viewed from an X-ray incidence direction to form a retreat space. The drive circuit board 12 is arranged in the retreat space and fastened to a fastening unit provided on the base 25 by screws and the like. In addition, a flexible wiring board 32 is folded or bent as illustrated. The flexible wiring board 32 is short because, unlike the flexible wiring board 31 on the side of the read circuit board 13, a large IC is not mounted on the board. When the flexible wiring board 32 is to be extended, the flexible wiring board 32 may be sandwiched between and fixed by the board and the base 25 in the same manner as the read circuit board 13. Moreover, a part of the structural body 26 may be retained in the same manner as in the case of the read circuit board 13 (FIGS. 8A and 8B).

In addition, the base 25 can be made of a non-metallic material such as CFRP. This is possible because even when a non-metallic material is used, the X-ray shielding member 24 can still fulfill the roles of an electromagnetic shield and an X-ray shield. The use of CFRP enables weight saving of the apparatus. This logic can also be applied to the second embodiment.

As described above, according to the third embodiment, a part of the structural body 26 is retreated to provide a space on an opposite side of the X-ray detection sensor 11 as viewed from an X-ray incidence direction, whereby circuit boards (12 and 13) are arranged in the space. Consequently, the sizes of the X-ray shielding member 24 and the base 25 can be reduced down to approximately the same size as the X-ray detection sensor 11, enabling further downsizing and weight saving of the apparatus.

[Fourth Embodiment]

Figure 9A:
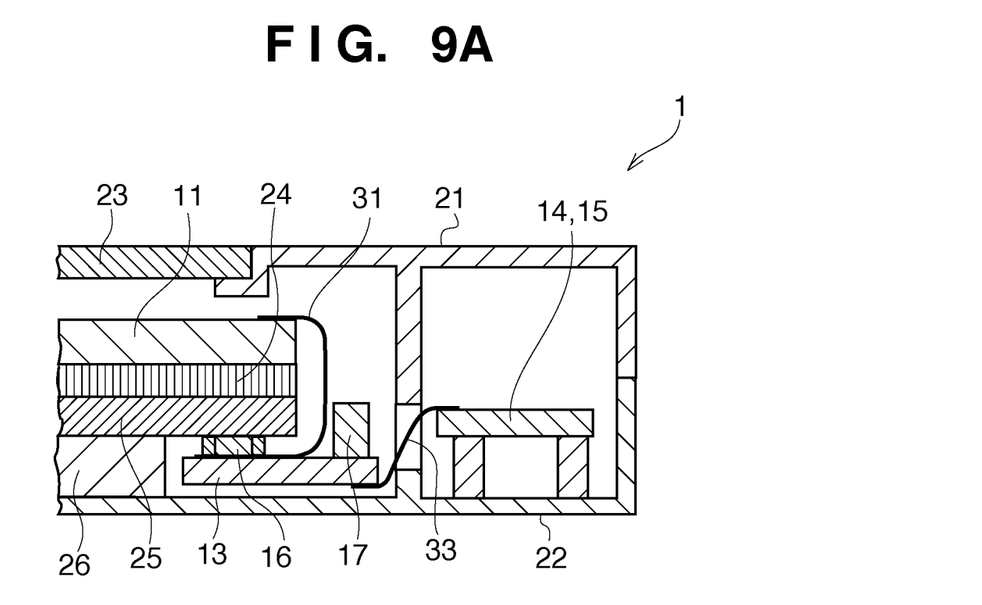
FIG. 9A is a cross-sectional view illustrating a configuration of an X-ray detection sensor according to a fourth embodiment.

FIG. 9A is a cross-sectional view of a radiographic apparatus according to a fourth embodiment. There are cases where circuit parts with a large height such as a capacitor 17 are mounted on a read circuit board 13 and a drive circuit board 12. In such cases, placing an entire board on an underside of an X-ray detection sensor results in an increase in thickness direction and poses a limit to achieving thinning When a mounted part with a large height is unaffected by X-rays, a circuit part is to be arranged by exposing a part of a circuit board to the outside of a projection plane of an X-ray detection sensor 11 as illustrated in FIG. 9A. Thinning of the apparatus can be achieved by adopting the structure according to the present embodiment.

[Fifth Embodiment]

Figure 9B:
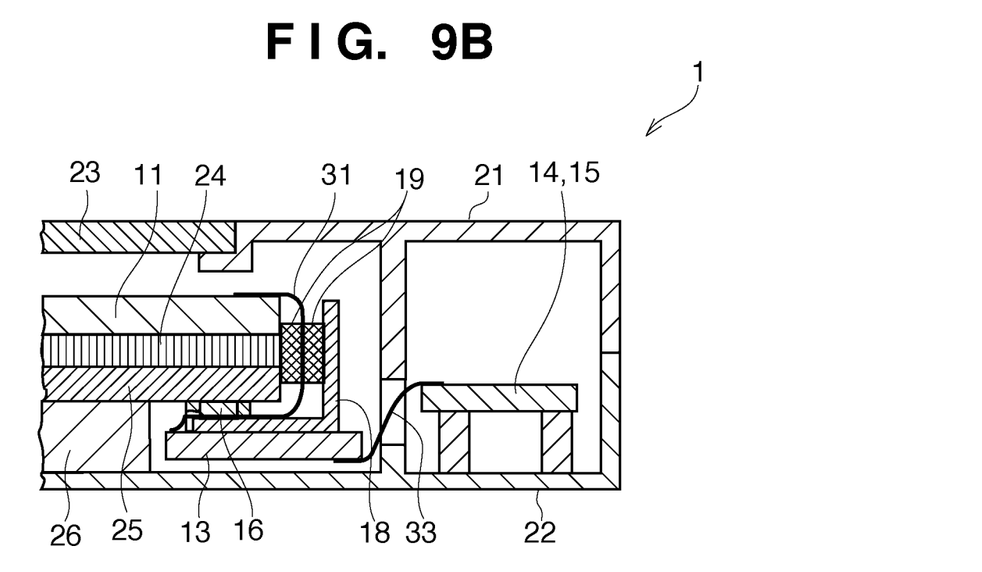
FIG. 9B is a cross-sectional view illustrating a configuration of an X-ray detection sensor according to a fifth embodiment.

FIG. 9B is a cross-sectional view of a radiographic apparatus 1 according to a fifth embodiment. Movement of a flexible wiring board 31 on a read circuit board 13 is restricted by a fixing plate 18 and a buffer material 19. The fixing plate 18 is a metallic plate. In the present example, aluminum is used as the material of the fixing plate 18. The fixing plate 18 has approximately the same length as the read circuit board 13 in a depth direction of FIG. 9B. An insulating sheet, not illustrated, is interposed between the fixing plate 18 and the read circuit board 13 and is insulated from the board. In addition, the buffer material 19 having cushioning characteristics is pasted onto the fixing plate 18 by adhesive tape or the like. The buffer material 19 is also pasted onto the side of an X-ray detection sensor 11 on an opposing side of the flexible wiring board 31 by adhesive tape or the like. By covering a path of the flexible wiring board 31 by a metallic plate, the effect of external noise can be reduced. Furthermore, by sandwiching the flexible wiring board 31 using the buffer material 19, the position of the flexible wiring board 31 can be stabilized and the fixing plate 18 and the flexible wiring board 31 can be prevented from coming into contact with each other. Moreover, the buffer material 19 prevents the flexible wiring board 31 from coming into contact with the X-ray detection sensor 11, a base 25, and an X-ray shielding member 24.

Therefore, favorable image quality unaffected by noise can be obtained by adopting the structure according to the fifth embodiment.

In addition, in the respective embodiments described above, the structural body 26 may be integrated with the base 25 by bonding or the like or the base 25 itself may constitute a structural body. Furthermore, the structural body 26 may be integrated with the second body 22 by bonding or the like or the second body itself may constitute a structural body.

Although preferred embodiments of the present invention have been described above, it is to be understood that the present invention is not limited to such embodiments and various modifications and changes may be possible without departing from the spirit and scope of the present invention.

According to the present invention, a radiographic apparatus can be provided which realizes weight saving, downsizing and thinning while protecting an interior X-ray detection sensor from external load and impact.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiographic apparatus comprising:
   an X-ray detection sensor having a two-dimensional detector plane for detecting an intensity distribution of X-rays;
   a body having an upper panel and a lower panel that opposes said upper panel, and internally containing said X-ray detection sensor;
   a supporting member having a supporting surface for supporting said X-ray detection sensor and fixed to said lower panel of said body;
   a read circuit board that reads out a detection signal from said X-ray detection sensor; and
   a signal processing circuit board that processes the detection signal read by said read circuit board;
   a power circuit board that supplies electrical power to said X-ray detection sensor;
   a handle portion which is used by a user when the user carries said radiographic apparatus; and
   a wall configured to divide said body into a first space on a side of the X-ray detection sensor and a second space on a side of the handle portion,
   wherein said first space internally contains said x-ray detection sensor and said reading circuit board, and said second space internally contains said signal processing circuit board and said power circuit board, and said signal processing circuit board and said power circuit board are located in a direction along said lower panel of said body.

2. The apparatus according to claim 1, further comprising an X-ray shielding member provided across an entire area of said supporting surface.

3. The apparatus according to claim 1, wherein a third space exists between a peripheral portion of said supporting member and said lower panel, and said read circuit board is located in said third space.

4. The apparatus according to claim 3, wherein said read circuit board is arranged so as to expose a portion of said read circuit board, on which is mounted a circuit part too big to be housed in said third space, to the outside of said third space.

5. The apparatus according to claim 3, further comprising a flexible wiring board on which a signal processing IC is mounted and which connects said read circuit board to said X-ray detection sensor, wherein a portion of said flexible wiring board on which said signal processing IC is mounted, is sandwiched between and fixed by said read circuit board and said supporting member in said third space.

6. The apparatus according to claim 5, further comprising a metallic plate provided along a path of said flexible wiring board so as to reduce effects of noise.

7. The apparatus according to claim 3, wherein said supporting member comprises:
   a plate-like base which includes said supporting surface; and
   a structural body which fixes said base by connecting said base to said lower panel,
   wherein said third space is formed between said base and said lower panel.

8. The apparatus according to claim 7, wherein said read circuit board is fixed to a face on an opposite side to said supporting surface of said base.

9. The apparatus according to claim 7, wherein said supporting surface of said base is larger in size than said X-ray detection sensor and larger than said structural body, and said third space is formed in a portion where said base protrudes from said structural body.

10. The apparatus according to claim 7, wherein said supporting surface of said base is equal in size to said X-ray detection sensor and larger than said structural body, and said third space is formed in a portion where said base protrudes from said structural body.

11. The apparatus according to claim 1, wherein signal processing circuit board and said power circuit board are separated from each other by a predetermined distance.

12. The apparatus according to claim 11, wherein said power circuit board and said signal processing circuit board are arranged with said handle portion in between.

13. A radiographic apparatus comprising:
   an X-ray detection sensor having a two-dimensional detector plane for detecting an intensity distribution of X-rays;
   a body having an upper panel and a lower panel that opposes said upper panel, and containing said X-ray detection sensor internally;
   a supporting member having a supporting surface for supporting said X-ray detection sensor and fixed to said lower panel of said body;
   a read circuit board which reads out a detection signal from said X-ray detection sensor;
   a signal processing circuit board which processes the detection signal read by said read circuit board;
   a power circuit board which supplies electrical power to said X-ray detection sensor; and
   a handle portion which is used by a user when the user carries said radiographic apparatus,
   wherein a space is formed between a peripheral portion of said supporting member and said lower panel, said read circuit board is located in said space, and said signal processing circuit board and said power circuit board are located in a direction along said lower panel in said read circuit board side and located separately so as to sandwich said handle portion.

14. A radiographic apparatus comprising:
   an x-ray detection sensor having a two-dimensional detector plane for detecting an intensity distribution of x-rays;
   a first body having an upper panel and a lower panel that opposes said upper panel and internally containing said x-ray detection sensor;

a supporting member having a supporting surface for supporting said x-ray detection sensor and fixing said x-ray detection sensor;
a reading circuit board that reads out a detection signal from said x-ray detection sensor;
a signal processing circuit board that processes the detection signal read by said reading circuit board;
a power circuit board that supplies electrical power to said X-ray detection sensor;
a handle portion which is used by a user when the user carries said radiographic apparatus; and
a second body having an upper panel and a lower panel that are opposing each other, which internally contains said signal processing circuit board and said power circuit board on a side of the handle portion, said signal processing circuit board and said power circuit board being located in a direction along said lower panel of said second body,
wherein said second body adjoins said first body.

* * * * *